United States Patent [19]

Tamaru et al.

[11] Patent Number: 4,599,465
[45] Date of Patent: Jul. 8, 1986

[54] PROCESS FOR PRODUCING ORTHOALKYLPHENOLS

[75] Inventors: Akio Tamaru; Yoshiaki Izumisawa, both of Kitakyushu; Hidekichi Hashimoto, Nakama; Kiyoji Kuma; Takashi Komaya, both of Kitakyushu; Masanobu Minagawa, Nakama, all of Japan

[73] Assignee: Mitsubishi Chemical Industries, Ltd., Tokyo, Japan

[21] Appl. No.: 741,361

[22] Filed: Jun. 5, 1985

[30] Foreign Application Priority Data

Jul. 5, 1984 [JP] Japan ................................. 59-139385

[51] Int. Cl.$^4$ .......................... C07C 39/06; C07C 37/14
[52] U.S. Cl. .................................... 568/781; 568/784; 568/789; 568/790; 568/794
[58] Field of Search ............... 568/790, 794, 789, 780, 568/781

[56] References Cited

U.S. PATENT DOCUMENTS

| 3,290,389 | 12/1966 | Hahn | 568/794 |
| 3,367,981 | 2/1968 | Napolitano | 568/789 |
| 3,670,030 | 6/1972 | Spark | 568/794 |
| 4,260,833 | 4/1981 | Firth | 568/789 |
| 4,398,048 | 8/1983 | Firth | 568/789 |

FOREIGN PATENT DOCUMENTS

| 2736059 | 2/1978 | Fed. Rep. of Germany | 568/794 |
| 7105596 | 10/1971 | France | 568/794 |
| 925819 | 5/1963 | United Kingdom | 568/794 |

Primary Examiner—Werren B. Lone
Attorney, Agent, or Firm—Oblon, Fisher, Spivak, McClelland & Maier

[57] ABSTRACT

A process for producing an orthoalkylphenol which comprises reacting phenol with an olefin in a liquid phase in the presence of an alumina catalyst, characterized in that the water content in the liquid phase of the reaction system is maintained at a level of not higher than 250 ppm.

14 Claims, No Drawings

PROCESS FOR PRODUCING ORTHOALKYLPHENOLS

The present invention relates to a process for producing an orthoalkylphenol by reacting phenol with an olefin.

An ortho-mono-alkylphenol is useful as an antioxidant or as an intermediate for the synthesis of agricultural chemicals, dyestuffs or the like. A process for producing an ortho-mono-alkylphenol by reacting a phenolic compound with an olefin in the presence of various catalysts has been known. For instance, U.S. Patent No. 3,290,389 discloses a process wherein $\gamma$-alumina is used as the catalyst. $\gamma$-alumina has no corrosive properties and easy to handle. It is therefore a desirable catalyst, but it has disadvantages that the catalytic activity deteriorates relatively quickly, and the conversion of phenol is thereby low. There have been some proposals for improvement to overcome the disadvantages. For instance, Japanese Examined Patent Publication No. 9663/1977 (U.S. Pat. No. 3,670,030) proposes to add water to the reaction system in order to prevent the quick deterioration of the catalytic activity or $\gamma$-alumina. This reference discloses that the quick deterioration of the catalytic activity in the reaction of a phenolic compound such as phenol or hydroxy anisole with an olefin such as isobutylene or 2-methyl butene-2, can be prevented by adding water in an amount of from 500 to 5000 ppm based on the phenolic compound.

However, as a result of the study by the present inventors, it has been found that in the liquid phase reaction of phenol with an olefin in the presence of $\gamma$-alumina as the catalyst, the catalytic activity increases when the amount of water in the reaction system is rather reduced. Namely, phenol is hygroscopic and readily absorbs moisture from air. As is evident from the fact that the industrial standards such as ASTM D-2439-68, permit a water content of maximum 0.20 weight % for Refined Phenol-405, commercially available phenol for industrial purposes contains moisture of the order of some hundreds or thousands ppm, usually from 300 to 2,000 ppm. Further, the alumina catalyst contains adsorbed water. Therefore, the moisture in the liquid phase of the reaction system reaches at least some hundreds ppm, for example, 500 to 5,000 ppm. The present inventors have found that no adequate activity of the alumina catalyst can be obtained in the reaction system having such a water content, but when the water content in the liquid phase is reduced to a certain predetermined level, the catalytic activity of the alumina catalyst is remarkably improved, and the selectivity for an ortho-mono-alkylphenol is also improved and the production of a dialkylphenol as a by-product can be reduced. Further, it has been found that the conversion and the selectivity are also substantially affected by the method for the preparation of the alumina catalyst.

It is an object of the present invention to provide a process for producing an ortho-mono-alkylphenol efficiently in good yield by activating the catalytic activity of an alumina catalyst in the liquid phase reaction of an olefin with phenol.

Such an object of the present invention can be obtained by a process for producing an ortho-mono-alkylphenol which comprises reacting phenol with an olefin in a liquid phase in the presence of an alumina catalyst, characterized in that the water content in the liquid phase of the reaction system is maintained at a level of not higher than 250 ppm based on the weight of the liquid phase.

Now, the present invention will be described in detail with reference to the preferred embodiments.

In the present invention, phenol and an olefin are reacted. As the starting material olefin, a $C_2$–$C_{20}$ olefin is usually employed. Specifically, there may be mentioned, for instance, ethylene, propylene, 1-butene ($\alpha$-butylene), $\beta$-butylene, isobutylene, $\alpha$-amylene, $\gamma$-amylene or $\beta$-isoamylene. Among them, secondary olefins capable of forming secondary carbonium ions (i.e. olefins of the formula $R^1$-HC=CH-$CR^2R^3R^4$, wherein each of $R^1$ to $R^4$ is a hydrogen atom or a hydrocarbon residue) such as propylene or 1-butene, are preferred. These olefins are used usually in an amount of from 0.1 to 10 mol per mol of phenol.

As the catalyst effective in the process of the present invention, an alumina catalyst is employed. Alumina having a catalytic activity is the one formerly called $\gamma$-alumina, and various methods for its preparation are known. For instance, there may be mentioned (1) an alumina prepared by hydrolyzing an aqueous sodium aluminate solution obtained by a Bayer's process, with carbon dioxide, then drying the precipitates thereby obtained, and calcining aluminum hydroxide thereby obtained, (2) an alumina prepared by hydrolyzing an aluminum alkoxide, and calcining aluminum hydroxide thereby obtained, (3) an alumina obtained by neutralizing an aqueous solution of an aluminum salt of an inorganic acid such as aluminum sulfate, aluminum nitrate or aluminum chloride, with an alkaline reagent such as aqueous ammonia or an aqueous sodium hydroxide solution, and calcining aluminum hydroxide thereby obtained, and (4) an alumina obtained by thermally decomposing the above-mentioned aluminum salt of an inorganic acid in air.

In the process of the present invention, aluminas prepared by the above-mentioned various conventional methods may be employed as the catalyst. Preferred is an alumina catalyst having a sodium and potassium content of not higher than 500 ppm, more preferably not higher than 100 ppm. By using such an alumina catalyst, good results are obtainable with respect to the conversion and the selectivity. In order to obtain such a catalyst having a low sodium and potassium content, it is preferred to employ the above-mentioned method (2).

Now, a preferred embodiment for the preparation of the alumina catalyst to be used in the process of the present invention, will be described.

An aluminium alkoxide of the formula $(Al(OR)_3$ wherein R is a $C_2$–$C_{30}$ alkyl group, such as aluminum ethoxide, aluminum isopropoxide, aluminium sec-butoxide or aluminum tert-butoxide, is dispersed in water of from 3 to 500 times by mol at a temperature of from 0° to 100° C., and aluminum hydroxide precipitates thereby obtained, are calcined at a temperature of from 400° to 1000° C., preferably from 500° to 700° C., for from 0.01 to 20 hours.

The amount of the catalyst used in the present invention is usually from 0.001 to 0.3 times as much as the weight of phenol, in the case where the reaction is conducted in a suspension type system. The catalyst is used usually in the form of powders or grains.

The reaction of phenol with an olefin is conducted usually at a temperature of from 150° to 400° C., preferably from 180° to 300° C. If the temperature is too low, the reaction rate will be slow, and if the temperature is too high, the formation of undesirable by-products tends to increase. The reaction is conducted under a pressure sufficient to maintain the starting phenol to be in a liquid state at the reaction temperature, usually under a pressure of from 1 to 50 kg/cm$^2$. The reaction time is usually from 0.1 to 50 hours in case of the reaction system where the catalyst is used in a suspension type.

The reaction of the present invention can be conducted in a batchwise system, a semi-continuous system or a continuous system. As a reaction method, there may be mentioned a method wherein a mixture of phenol and an olefin is passed through a fixed bed packed with the catalyst under the reaction conditions, or a method wherein the catalyst is suspended in phenol, and an olefin is supplied under the reaction conditions to conduct the reaction for a predetermined period of time. The reaction of the present invention is usually conducted without using any special solvent. However, an optional organic solvent may be employed, as the case requires.

After the reaction, it is usual to separate the catalyst from the reaction mixture by e.g. filtration, and then the reaction mixture is subjected to distillation by a conventional method, whereby the desired ortho-mono-alkylphenol can be recovered.

In the present invention, it is essential that at the time of the reaction of phenol with an olefin, the water content in the liquid phase of the reaction system be maintained at a level of not higher than 250 ppm, preferably not higher than 200 ppm, more preferably not higher than 150 ppm based on the weight of the liquid phase. Namely, the starting phenol is hygroscopic, and commercially available phenol usually contains from 300 to 2,000 ppm of water, and the alumina catalyst also contains water as it adsorbs moisture as time passes after its preparation. Therefore, if such phenol and alumina catalyst are used as they are, the water content in the liquid phase of the reaction system will be at a level of at least some hundreds ppm. Therefore, in the present invention, it is necessary to preliminarily remove water from phenol and the catalyst so that the water content in the liquid phase of the reaction solution will be not higher than 250 ppm.

The water removal treatment from starting phenol may be carried out by using such methods as distillation, a blowing an inert gas such as nitrogen or argon into heated phenol, or a treatment with a water-absorbing agent such as molecular sieve, zeolite, alumina or ion exchange resins. Water removal treatment of the alumina catalyst is usually conducted by heating it prior to its use. Particularly preferred for the practical operation is a method wherein the starting material phenol and alumina catalyst are mixed and heated, and then an inert gas is blown into the heated mixture for water removal; a method wherein a mixture of the phenol and catalyst is heated to distillation, or a method wherein an inert gas is supplied during the distillation under heating. In these methods, the water removal from phenol and alumina is carried out simultaneously, and the reaction of phenol with an olefin can be conducted immediately after the water removal by supplying the olefin into the mixture of the phenol and catalyst after the water removal.

A preferred embodiment of the present invention will be specifically described as follows.

Into a reactor provided with a distillation column, phenol and the alumina catalyst are charged, and the mixture is heated for distillation by conventional method. The distillation is carried out under substantially atmospheric pressure and under this condition, the distillation temperature may be from about 140° to 185° C. The distillation may also be carried out under reduced pressure or increased pressure. As to the distillation column, universal columns such as a perforated plate column, a packed column and the like can be used as they are or after adjusted adequately. The distillation is generally conducted under reflux. To remove the water efficiently with lower phenol distillation, the greater the reflux ratio, the better the distillation, and the suitable reflux ratio is determined also in consideration to heat energy to be required, cost for recovery of distillate and the like. In some cases, distillation may be carried out under total reflux with continuous or intermittent discharge of phenol having higher water content which is accumulated at the top of the column. The discharged phenol may be recovered after separation of water and reused as starting material.

By the above operation, when the water content in phenol has been reduced to a desired level, the distillation is terminated, and the alkylation reaction is initiated by supplying an olefin to the reactor.

After the completion of the reaction, only the liquid phase is removed from the reactor after being separated from the catalyst by filtration or sedimentation and is distilled to obtain the desired ortho-mono-alkylphenol. The separated catalyst can be reused until the catalytic activity will be lost. So the fresh phenol is charged again into the reactor and the water removal treatment is effected as above, then an olefin is supplied to repeat the above-mentioned operation. In other case, after the reaction is completed, the slurry of reaction mixture is removed from the reactor, and liquid phase is separated from the catalyst by filtration and is distilled to obtain the desired ortho-mono-alkylphenol. In this case, fresh phenol is charged into the reactor and water removal treatment of fresh phenol is carried out, then the separated catalyst as above is added thereto, and the alkylation reaction is repeated by introduction of an olefin.

According to the process of the present invention, by adjusting the water content in the liquid phase of the reaction system to a level of not higher than 250 ppm, the catalytic activity of the alumina catalyst can be remarkably improved, the conversion of phenol and the selectivity for the ortho-mono-alkylphenol substantially increase, and the desired ortho-mono-alkylphenol can be obtained in good yield.

Further, by using an alumina catalyst having a small sodium and potassium content, the activity of the catalyst can be improved further.

Now, the present invention will be described in further detail with reference to Examples. However, it should be understood that the present invention is by no means restricted by these specific Examples.

EXAMPLES 1 TO 4 AND COMPARATIVE EXAMPLES 1 TO 3

Into a 1 liter autoclave equipped at its top with a distillation column, 500 g (5.31 mol) of phenol, a commercially available reagent grade (water content: 300 ppm), and an alumina catalyst (water content: 2.5% by weight) of the proportion as in Table 1, were charged, and the mixture was heated to about 185° C. for distillation. The distillation was conducted till the water content in the liquid phase of the reaction system reached to the level as in Table 1.

In Comparative Example 3, no water removal treatment by distillation was conducted.

Then, propylene was supplied to maintain the total pressure at a level of 4 kg/cm$^2$.G, and the reaction was conducted at 220° C. until the conversion of phenol reached substantially to a predetermined level, whereby the reaction time to be required, the selectivities of the desired product, i.e. ortho-isopropylphenol (OIPP) and the by-product, i.e. 2,6- or 2,4-diisopropylphenol (DIPP), were measured by gas chromatographic analysis. The results thereby obtained are shown in Table 1.

As the alumina catalyst, commercially available alumina hydrate prepared by the hydrolysis of an aluminum alkoxide Al(OR)$_3$ (R=C$_2$–C$_{30}$), followed by drying (trade name: Pural-SB, manufactured by Condea Chemie, which contains 0.008% of SiO$_2$, 0.005% of Fe$_2$O$_3$, 0.004% of Na$_2$O and 0.4% of carbon, as impurities) was used, after it was calcined at 600° C. for 4 hours in air.

TABLE 1

| | Water content (ppm) | Catalyst concentration (mol %) | Conversion of phenol (%) | Reaction time (min) | Selectivity (%) OIPP | DIPP |
|---|---|---|---|---|---|---|
| Example 1 | 55 | 2.0 *1 | 69.4 | 20 | 97.1 | 2.8 |
| Example 2 | 100 | 2.0 | 68.8 | 60 | 96.1 | 3.8 |
| Example 3 | 105 | 5.0 *2 | 70.6 | 25 | 95.9 | 4.0 |
| Example 4 | 195 | 5.0 | 68.2 | 70 | 95.2 | 4.7 |
| Comparative Example 1 | 390 | 5.0 | 69.0 | 180 | 94.3 | 5.6 |
| Comparative Example 2 | 505 | 5.0 | 71.0 | 240 | 93.7 | 6.2 |
| Comparative Example 3 | 1020 | 5.0 | 70.2 | 720 | 92.6 | 7.3 |

TABLE 1-continued

| | Water content (ppm) | Catalyst concentration (mol %) | Conversion of phenol (%) | Reaction time (min) | Selectivity (%) OIPP | DIPP |
|---|---|---|---|---|---|---|

*1 2.0 mol % = 2.17% by weight
*2 5.0 mol % = 5.42% by weight

From the above results, it is evident that in the case of the Examples of the present invention, the conversion of phenol reaches to about 70% in a short period of reaction time as compared with the Comparative Examples, and yet the selectivity for the by-product DIPP is low and the selectivity for the desired product OIPP is high.

EXAMPLE 5 AND COMPARATIVE EXAMPLE 4

The reaction was conducted in the same manner as in Example 1 except that 1-butene was employed instead of propylene as the olefin. The results are shown in Table 2. In Table 2, OSBP indicates the desired product, i.e. ortho-sec-butylphenol, and DSBP indicates the by-product i.e. 2,6- or 2,4-di-sec-butylphenol.

TABLE 2

| | Water content (ppm) | Catalyst concentration (mol %) | Conversion of phenol (%) | Reaction time (min) | Selectivity (%) OSBP | DSBP |
|---|---|---|---|---|---|---|
| Example 5 | 110 | 5.0 | 70.4 | 65 | 98.2 | 1.8 |
| Comparative Example 4 | 520 | 5.0 | 69.3 | 600 | 95.6 | 4.4 |

EXAMPLES 6 to 8 AND COMPARATIVE EXAMPLES 5 TO 7

Phenol and propylene were reacted in the same manner as in Example 1 except that the catalysts prepared by the following methods were employed. The results are shown in Table 3.

Catalyst A

An aqueous sodium aluminate solution obtained by a Bayer's process was hydrolyzed with carbon dioxide, and the resulting precipitates were dried to obtain aluminum hydroxide, which was then calcined to obtain an alumina. Na and K content: 220 ppm.

Catalyst B 200 g of aluminum sulfate (Al$_2$(SO$_4$)$_3$.14–18H$_2$O) was dissolved in 1 liter of water. To this solution, 10 wt. % of aqueous ammonia solution was dropwise added until the pH reached 7, and the resulting aluminum hydroxide was washed, then dried at 120° C., and calcined at 600° C. for 4 hours in air to obtain an alumina. Na and K content: 150 ppm.

Catalyst C

To 200 g of aluminum isopropoxide, a commercially available reagent grade, 10 times of water (about 2 liters) was added, and heated to 80° C. for hydrolysis. Then, isopropanol was distilled off, and the residue was dried at 120° C. and further calcined at 660° C. for 4 hours in air to obtain an alumina. Na and K content: 20 ppm.

TABLE 3

| | Catalyst | Water content (ppm) | Catalyst concentration (mol %) | Conversion of phenol (%) | Reaction time (min) | Selectivity (%) OIPP | DIPP |
|---|---|---|---|---|---|---|---|
| Example 6 | A | 95 | 5.0 | 67.7 | 80 | 93.0 | 6.9 |
| Comparative Example 5 | A | 505 | 5.0 | 70.1 | 900 | 90.2 | 9.6 |
| Example 7 | B | 100 | 5.0 | 71.2 | 120 | 92.0 | 7.9 |
| Comparative Example 6 | B | 495 | 5.0 | 68.5 | 1200 | 89.2 | 10.6 |
| Example 8 | C | 105 | 2.0 | 71.6 | 45 | 95.8 | 4.1 |
| Comparative Example 7 | C | 500 | 5.0 | 72.1 | 180 | 93.9 | 6.0 |

From the results in Table 3, it is evident that the reduction of the water content in the reaction system is effective regardless of the method for the preparation of the alumina catalyst. It is also evident that when the water content is low, the smaller the Na and K content in the alumina catalyst, the better the catalytic activity.

EXAMPLE 9

Commercially available phenol for industrial purposes (water content: 300 ppm) was passed through the column of Molecular sieve 4A (trade name, made by Gaskuro Kogyo Co.) to reduce the water content to a level of 55 ppm. The catalyst used in the reaction in Example 1 was recovered, and reused as it is, as the catalyst. By using such phenol and alumina catalyst, the reaction was conducted in the same manner as in Example 1. The results are shown in Table 4.

TABLE 4

| | Water content (ppm) | Catalyst concentration (mol %) | Conversion of phenol (%) | Reaction time (min) | Selectivity (%) OIPP | DIPP |
|---|---|---|---|---|---|---|
| Example 9 | 50 | 2.0 | 71.6 | 20 | 96.9 | 3.0 |

We claim:

1. A process for synthesizing an o-monoalkylphenol, which comprises:
   reacting phenol with a $C_2$–$C_{20}$ olefin at a temperature of 150°–400° C. in the liquid phase in the presence of an alumina catalyst while maintaining the water content at a level of not higher than 250 ppm.

2. The process according to claim 1, wherein the olefin is propylene or 1-butene.

3. The process according to claim 1, wherein the water content is not higher than 200 ppm.

4. The process according to claim 1, wherein the water content is not higher than 150 ppm.

5. The process according to claim 1, wherein the sodium and potassium content in the alumina catalyst is not higher than 500 ppm.

6. The process according to claim 5, wherein the catalyst is an alumina prepared by calcining aluminum hydroxide obtained by the hydrolysis of an aluminum alkoxide.

7. The proccess according to claim 1, wherein the amount of said catalyst in the reaction medium ranges from 0.001 to 0.3 times as much as the weight of phenol.

8. The process according to claim 1, wherein the reaction temperature ranges from 180° to 300° C.

9. The process according to claim 1, wherein the reaction is conducted at a pressure of 1 to 50 kg/cm².

10. A process for synthesizing an o-monoalkylphenol, which comprises:
    heating phenol or a mixture of phenol and an alumina catalyst to distill the liquid medium until the water content of the phenol is reduced to a level not higher than 250 ppm;
    adding a $C_2$–$C_{20}$ olefin to the liquid phenol medium; and
    reacting the ingredients within the phenol medium to effect said synthesis.

11. The process according to claim 10, wherein the olefin is propylene or 1-butene.

12. The process according to claim 10, which further comprises passing an inert gas into the phenol being distilled in the first step.

13. The process according to claim 10, wherein the temperature of distillation ranges from 140° to 185° C.

14. The process according to claim 10, wherein said distillation is conducted under reduced or increased pressure.

* * * * *